United States Patent
Trom et al.

(10) Patent No.: US 6,293,796 B1
(45) Date of Patent: Sep. 25, 2001

(54) DENTAL MATRIX CLAMP FOR TOOTH RESTORATION PROCEDURES

(75) Inventors: Matthew C. Trom, Cottage Grove; Byron Ciping Shen, Woodbury; John W. Dubbe, Oakdale, all of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/427,901

(22) Filed: Oct. 27, 1999

(51) Int. Cl.7 .................................................. A61C 5/04
(52) U.S. Cl. ............................................ 433/155; 433/139
(58) Field of Search ..................................... 433/155, 139

(56) References Cited

U.S. PATENT DOCUMENTS

| | | | |
|---|---|---|---|
| 164,870 | 6/1875 | Palmer | 433/139 |
| 532,723 | 1/1895 | Dennis | 433/162 |
| 644,705 | 3/1900 | Evans | 433/40 |
| 677,268 | 6/1901 | Power | 433/40 |
| 692,274 | 2/1902 | Gumaer | 24/537 |
| 867,379 | 10/1907 | Kaufmann | 24/264 |
| 1,378,748 | 5/1921 | Wiggins | 433/162 |
| 2,083,077 | 6/1937 | Mayer | 24/341 |
| 2,088,208 | 7/1937 | Kassap | 24/72.5 |
| 2,567,101 | 9/1951 | Carpenter | 433/39 |
| 2,646,622 | 7/1953 | Christie et al. | 433/39 |
| 2,651,841 | 9/1953 | Peterson | 433/162 |
| 2,663,935 | 12/1953 | Walser | 433/39 |
| 2,790,238 | 4/1957 | Trangmar | 433/39 |
| 3,074,169 | 1/1963 | Freeman | 433/39 |
| 3,108,377 | 10/1963 | Meyer | 433/39 |
| 3,463,157 | 8/1969 | Hunt | 606/158 |
| 3,517,444 | 6/1970 | Tofflemire | 433/158 |
| 3,548,500 | 12/1970 | Cohen | 433/218 |
| 3,628,249 | 12/1971 | Wurl | 433/40 |
| 3,699,595 | 10/1972 | Tofflemire | 433/39 |
| 4,269,190 | 5/1981 | Behney | 606/158 |
| 4,303,389 | 12/1981 | Salsarulo | 433/40 |
| 4,787,849 | 11/1988 | Jacoby et al. | 433/139 |
| 4,824,365 | 4/1989 | von Weissenfluh | 433/40 |
| 4,986,752 | 1/1991 | Graves | 433/138 |
| 5,527,181 | 6/1996 | Rawls et al. | 433/149 |
| 5,584,692 | 12/1996 | Weissenfluh et al. | 433/155 |
| 5,607,302 | 3/1997 | Garrison et al. | 433/39 |
| 5,622,496 | 4/1997 | Champagne | 433/39 |
| 5,730,592 | 3/1998 | Meyer | 433/39 |
| 5,788,487 | 8/1998 | Meyer | 433/39 |
| 5,890,900 | 4/1999 | Fischer et al. | 433/149 |
| 5,890,901 | 4/1999 | Fischer et al. | 433/149 |
| 5,944,729 | * 8/1999 | Blake | 606/139 |

FOREIGN PATENT DOCUMENTS 292585   8/1953   (CH) .

OTHER PUBLICATIONS

Clinical Research Associates Newsletter, Nov. 1997, V.ol. 21, Issue 11.

* cited by examiner

Primary Examiner—John J. Wilson
(74) Attorney, Agent, or Firm—James D. Christoff

(57) ABSTRACT

A matrix clamp used in dental procedures to restore teeth to their natural shapes has a pair of gripping portions that are each connected to a cross-over bar. When the gripping portions are depressed by finger pressure, a pair of clamping tines connected to the cross-over bars spread apart from each other to enable the tines to be placed in contact with a sectional matrix band. When the gripping portions are released, a coil spring portion of the matrix clamp urges the tines toward each other so that the sectional matrix band is secured against the tooth and the clamp is retained in its selected position.

13 Claims, 2 Drawing Sheets

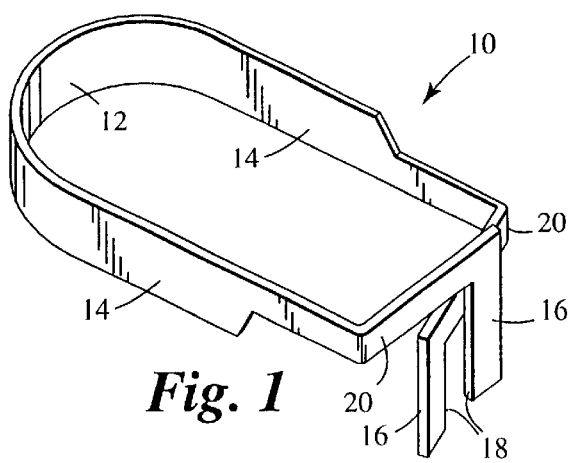
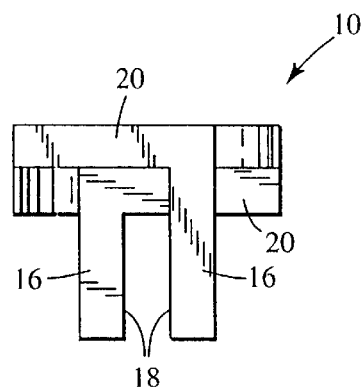
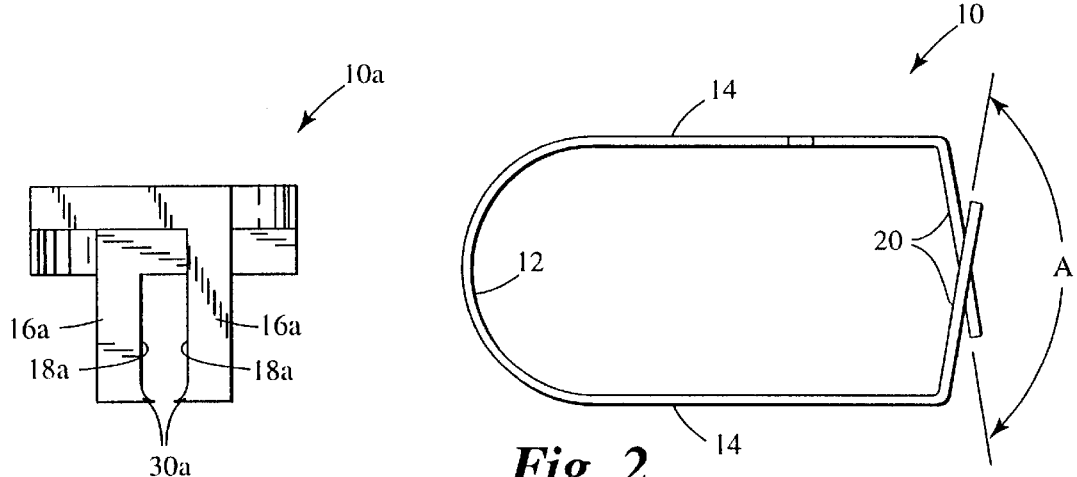
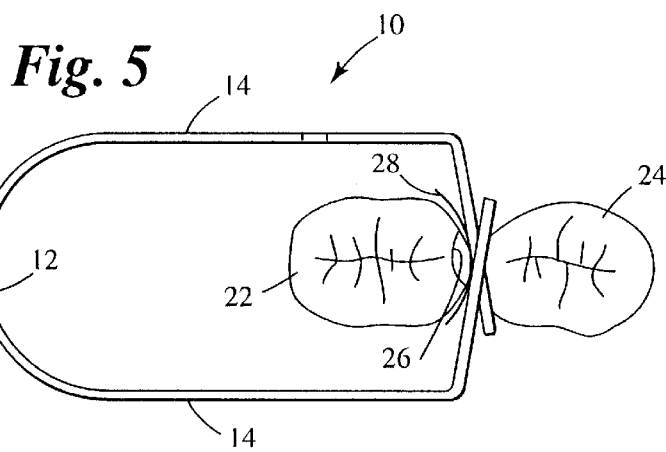
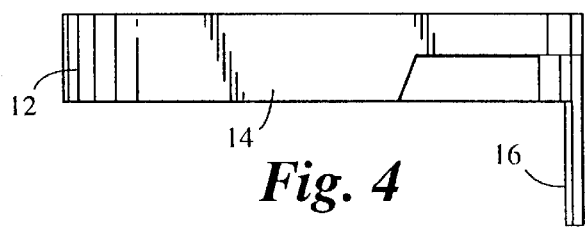

DENTAL MATRIX CLAMP FOR TOOTH RESTORATION PROCEDURES

BACKGROUND OF THE INVENTION

1. Field of the Invention

This invention broadly relates to a matrix clamp used in dental procedures. More particularly, the present invention is directed toward a clamp used to hold a matrix band against a tooth while a restorative material is placed in a tooth cavity and while the material hardens.

2. Description of the Related Art

The practice of dentistry often involves treatment of teeth that have developed cavities. Cavities frequently result from a process of dental decay, where acids from food or bacteria dissolve the tooth enamel. If the cavity is not treated, the decay will continue to progress through the enamel and into the dentin.

To treat a tooth having a cavity, the practitioner typically removes the decayed portions of the tooth and then places a restorative material in the cavity. Dental restorative materials, also known as fillings, can be made of a composite material, a silver amalgam or gold. After the restorative material is packed into the prepared cavity, the material is shaped or carved by the practitioner to a configuration that preferably resembles the original shape of the tooth.

In some instances, such as when the cavity is relatively small and located in the middle of the occlusal surface (i.e., the outer or biting surface) of the bicuspid or molar teeth, the restorative material can be placed into the cavity and held in place by surrounding tooth structure until such time as the restorative material hardens. However, in other instances there may be insufficient tooth structure to securely hold the restorative material in place during placement and hardening. For example, if the cavity is located wholly or partially along one or more sides of the tooth, there may be insufficient adjacent tooth structure to hold the restorative material in place during the time that the restorative material is packed into the cavity by the practitioner and subsequently during the time that the restorative material is hardened.

As a consequence, dental practitioners often use a matrix band or a sectional matrix band to act as an auxiliary support that holds the restorative material in place during packing and hardening. Matrix bands and sectional matrix bands serve a function somewhat similar to formwork used when pouring concrete, in that the band provides an additional surface that helps to retain the restorative material in the cavity during placement, packing and hardening. Once the material has sufficiently hardened, the band is removed from the oral cavity and the surface of the restorative material that extends along areas where the band was previously located can be shaped or smoothed as needed to better blend in with the adjacent tooth surfaces.

Oftentimes, small dental wedges are placed in the interproximal spaces between the matrix band (or sectional matrix band) and the tooth adjacent the tooth that contains the cavity. The wedge serves to help retain the band in place and also helps urge the decayed tooth away from the adjacent tooth during the dental procedure. It is desirable to provide such a spacing during the restorative procedure, so that once the procedure is finished and the wedge and band are removed, the surface of the restorative material closely contacts the adjacent tooth.

While a variety of matrix band systems have been proposed in the past, there are generally two types of systems in current widespread use. One type of system includes an elongated matrix band and a clamp that is connected to opposite ends of the band. The band is placed around the circumference of the tooth and the clamp is then tightened to apply tension to both ends of the band, thereby pulling the band into place around the tooth. The clamp may include a screw mechanism that can be turned as desired to tighten the band against the sides of the tooth. Examples of such systems are described in U.S. Pat. No. 5,622,496 to Champagne and U.S. Pat. No. 3,517,444 to Tofflemire.

Another type of matrix band system includes a sectional matrix band. Sectional matrix bands typically extend only partially around the circumference of the tooth, and are most often placed in the interproximal regions (i.e., the regions directly adjacent neighboring teeth). The sectional matrix band is frequently held in place by one or more spring clamps that provide pressure against the band and adjacent tooth structure.

Sectional matrix bands are often made of a thin strip of plastic material or of metallic material such as stainless steel. The metallic material is preferably flexible and resilient, so that it can assume a curved shape that closely matches the original curved shape of the sides of the tooth. In some instances, the sectional band may be trimmed by the dental practitioner to better fit the interproximal space.

Conventional spring clamps used with sectional matrix bands are often made of a circular spring metal body and a pair of depending jaws or legs. The circular body has an inherent spring memory that urges the legs toward each other. To use the clamp, a specially-adapted pair of dental pliers is used to open the spring body against its inherent tension and move the legs apart from each other. Once the legs are placed in position straddling the interproximal area adjacent the wedge and band, the force on the pliers is released and the spring tension of the body then moves the legs toward each other and into a position in contact with the band and the wedge.

Once the spring clamp is properly placed, the legs of the clamp hold the band against the lingual side of the tooth (i.e., the side of the tooth facing the patient's tongue) next to the interproximal area and also against the buccolabial side of the tooth (i.e., the side of the tooth facing the patient's cheeks or lips) next to the interproximal area. In that position, the legs also bear against the wedge, which serves to slightly separate the decayed tooth from the adjacent tooth located on the other side of the wedge.

While the matrix band systems described above have been somewhat satisfactory in the past, there is a continuing need in the art to improve such systems. More particularly, it would be desirable to provide a matrix clamp for sectional matrix bands that is inexpensive and easy to use, and yet eliminates the need to use a separate hand instrument for placement of the clamp. It would also be preferable to avoid use of the dental wedge in the procedure if at all possible.

SUMMARY OF THE INVENTION

The present invention is directed toward a dental matrix clamp that has a cross-over clamping movement for securing a sectional matrix band in place. The practitioner grips the clamp during use and applies finger pressure to opposite sides of the clamp to spread a pair of elongated tines apart from each other. The cross-over clamping movement enables the tines to be moved apart from each other by finger pressure and without the use of hand instruments or the like. Once finger pressure on the clamp is released, the tines move toward each other to snugly fit between the band and the adjacent tooth.

In more detail, the present invention is directed toward a dental matrix clamp for tooth restorative procedures and comprises a coil spring portion made of a resilient material. The clamp also includes a pair of spaced apart gripping portions each connected to the coil spring portion. The gripping portions and the coil spring portion extend in a generally common reference plane. The clamp also includes a pair of elongated tines each having an elongated clamping edge, wherein the clamping edges extend along generally parallel paths. The clamp also has a pair of cross-over bars extending past each other along laterally adjacent paths. Each cross-over bar couples one of the tines to one of the gripping portions. The coil spring portion is biased to urge the clamping edges in directions toward each other. The clamping edges of the tines extend in directions generally perpendicular to the reference plane to engage opposite sides of an interproximal region between two adjacent teeth in an oral cavity.

In preferred embodiments of the invention, the elongated clamping edges of the tines have tapered or wedge-like shapes. One side of each clamping edge can be placed into contact with the sectional band while the opposite side of the clamping edge contacts the adjacent, non-decayed tooth. The wedge-shaped clamping edges help to urge the decayed tooth away from the adjacent tooth, such that use of a separate dental wedge may be avoided.

These and other aspects of the invention are described in more detail in the paragraphs that follow and are illustrated in the accompanying drawings.

BRIEF DESCRIPTION OF THE DRAWINGS

FIG. 1 is a perspective view of a dental matrix clamp made in accordance with one embodiment of the present invention;

FIG. 2 is a reduced bottom plan view of the matrix clamp shown in FIG. 1;

FIG. 3 is an end elevational view of the matrix clamp shown in FIGS. 1 and 2;

FIG. 4 is a side elevational view of the matrix clamp shown in FIGS. 1–3;

FIG. 5 is a top plan view of the dental matrix clamp shown in FIGS. 1–4 along with a portion of a dental arch and a sectional matrix band, showing one example of how the matrix clamp may be used to hold the sectional matrix band in place in an interproximal region between two adjacent teeth during a dental restorative procedure;

FIG. 6 is a view somewhat similar to FIG. 3 but showing a dental matrix clamp with tines constructed in accordance with another embodiment of the invention;

DETAILED DESCRIPTION OF THE PREFERRED EMBODIMENTS

Figure 7:
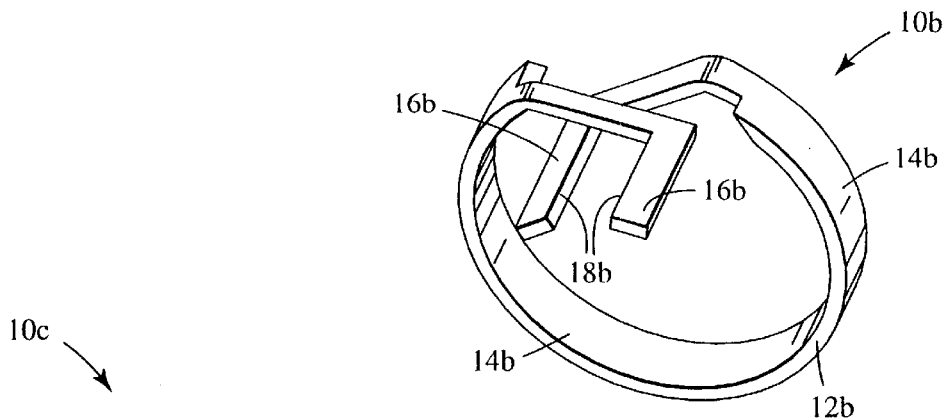
FIG. 7 is a perspective view of a dental matrix clamp shown in accordance with another embodiment of the invention.

A matrix clamp for dental restorations is broadly designated by the numeral 10 in FIGS. 1–4. The clamp 10 includes a coil spring portion 12 that, in this embodiment, has a half-coil configuration or "C"-shaped configuration. The coil spring portion 12 is made of a resilient material having inherent memory.

The matrix clamp 10 also includes a pair of spaced apart gripping portions 14. A rear end section of each gripping portion 14 is connected to front leg sections of the coil spring portion 12. Preferably, but not necessarily, the longitudinal axes of the gripping portions 14 extend along parallel paths when the clamp 10 is in the orientation as shown in FIGS. 1–3.

Optionally, the gripping portions 14 are provided with structure to enhance the user's grip on the clamp 10. For example, the gripping portions 14 may be provided with a knurled surface or roughened surface. Other options include protrusions, cavities, and/or non-slip coatings.

The clamp 10 also includes a pair or elongated tines 16, each of which has an elongated clamping edge 18 (see, e.g., FIGS. 1 and 3). Optionally, each tine 16 lies in a reference plane that is generally perpendicular to the longitudinal axes of the adjacent gripping portion 14. In the illustrated embodiment, each of the tines 16 has a flat shape that extends in a respective reference plane. Optionally, each tine 16 may extend at an obtuse angle relative to the longitudinal axis of the adjacent gripping portion 14 when viewing FIG. 4.

When the clamp 10 is in the orientation shown in FIG. 2, the reference planes containing the tines 16 are oriented at an angle designated "A" in FIG. 2. Preferably, the angle "A" is in the range of about 140 degrees to about 180 degrees. An example of a suitable angle "A" is about 160 degrees. However, other angles "A" may also be employed. For example, the angle A may be selected to provide maximum, face-to-face contact between the side of the tines 16 and the tooth to be restored.

The clamp 10 also includes a pair of cross-over bars 20 that extend past each other along laterally adjacent paths. Each cross-over bar 20 has a rear end section that is connected to a front end section of a respective gripping portion 14. Each cross-over bar 20 also has a forward section that is connected to an upper section of a respective tine 16.

The gripping portions 14 and the coil spring portion 12 extend in a generally common reference plane. Preferably, the cross-over bars 20 also extend in that same plane. The clamping edges 18 and preferably also the longitudinal axes of the tines 16 extend in directions generally perpendicular to that reference plane.

The tine 16 preferably have a wedge-shaped cross-sectional configuration when viewed in reference planes transverse to their longitudinal axes, such that the tines 16 narrow as the clamping edge 18 is approached. As an alternative, however, the tines 16 may have rectangular cross-sectional configuration in such reference planes and present a generally flat clamping edge 18. Other possible cross-sectional shapes include circular, oval or square, and/or a shape that matches the cross-sectional shape of other regions of the clamp 10. As another alternative, the tines 16 may include protrusions in one or more directions or other structure on or near the clamping edges 18, including in areas on or near the outermost end of the clamping edges 18 remote from the cross-over bars 20, to facilitate retaining the clamp 10 and matrix band in place during a dental procedure.

Preferably the clamp 10 is made from a unitary section of resilient material such as spring steel, plastic or composite materials. The clamp is preferably made of a material that can be resterilized a number of times for multiple uses without adversely affecting its resilient characteristics. An example of a particularly preferred material is stainless steel spring stock.

An example of use of the clamp 10 is illustrated in FIG. 5, wherein a first molar tooth 22 and a second molar tooth 24 are depicted for purposes of illustration (other teeth in the dental arch are not shown in the drawing). The molar tooth 22 has a cavity 26 located on its distal side (i.e., on a side facing away from the middle of the patient's dental arch). The cavity 26 is located in an interproximal area and is directly adjacent a mesial side of the second molar tooth 24 (i.e., a side facing the middle of the patient's dental arch).

Once the practitioner has removed decayed matter from the cavity 26 and has prepared the cavity 26 to receive a restorative material, a sectional matrix band 28 is inserted between the first molar tooth 22 and the second molar tooth 24 adjacent the distal side of the cavity 26. Optionally, the sectional matrix band 28 may be trimmed by the practitioner to facilitate placement and/or shaping of the restoration.

Next, the clamp 10 is placed in the oral cavity to securely hold the sectional matrix band 28 in place. To install the clamp 10, the practitioner grasps the gripping portions 14 between his or her thumb and a finger of the same hand such as a forefinger. Finger pressure is then exerted on the gripping portions 14 to move the gripping portions 14 toward each other. As the gripping portions are moved in this manner, the cross-over bars 20 enable the tines 16 to move away from each other and toward the orientation shown in FIG. 1.

Once the clamping edges 18 have been moved apart a sufficient distance for placement, the clamp 10 is maneuvered in the oral cavity to bring the tines 16 into positions extending along the lingual and buccolabial sides of the interproximal area respectively. Next, the practitioner relaxes his or her grip on the gripping portions 14 to cause the clamping edges 18 to move into a position in contact with the sectional matrix band 28. If the clamp 10 is properly placed, the clamping edges 18 contact both the distal side of the sectional matrix band 28 and mesial side portions of the second molar tooth 24 as shown in FIG. 5.

The coil spring portion 12 of the matrix clamp 10 has inherent memory that urges the tines 16 toward each other with sufficient force such that the clamping edges 18 tightly retain the sectional matrix band 28 in secure contact with distal side portions of the first molar tooth 22 during placement of the dental restorative material in the cavity 26 and also during the time that the restorative material hardens. Preferably, the coil spring portion 12 urges the tines 16 together with sufficient force to slightly shift the teeth 22, 24 away from each other, so that the distal side of the completed restoration is in a proper orientation relative to the mesial side of the second molar tooth 24. As such, the present invention avoids the need to use a dental wedge in many instances.

As can be appreciated, use of the matrix clamp 10 is a significant advantage over past practices in that the matrix clamp 10 can be installed and removed as desired without the use of hand instruments such as specially-adapted dental pliers or the like. Additionally, the matrix clamp 10 can be installed in the oral cavity with only one hand, leaving the practitioner's other hand free to do other tasks as needed.

The example shown in FIG. 5 can also be reversed, such that the matrix band 28 and the tooth to be restored are located outboard (i.e., external) of the tines 16. As another option, the clamp 10 may be used to hold two matrix bands in place between two teeth having adjoining, interproximal cavities. Additionally, while the foregoing discussion mentions use of the clamp 10 to restore teeth with cavities having decayed structure, it should be understood in this regard that the clamp 10 also may be used to restore tooth structure that has been broken or chipped.

In FIGS. 1–4, the matrix clamp 10 is not shown in its relaxed or "normal" orientation. Instead, the matrix clamp 10 is depicted as it appears when the gripping portions 14 are squeezed partially together, in order to better illustrate the tines 16 and the clamping edges 18. When pressure on the gripping portions 14 is released after use, the matrix clamp 10 self-returns to a relaxed orientation where the clamping edges 18 contract each other.

A dental matrix clamp 10a according to another embodiment of the invention is illustrated in FIG. 6. Except for the differences noted below, the dental matrix clamp 10a is identical to the dental matrix clamp 10 described above and as a consequence a detailed description of such common features need not be repeated.

The dental matrix clamp 10a has a pair of elongated tines 16a that are somewhat similar to the tines 16, except that each of the tines 16a has an outermost projection 30a. The projections 30a extend toward each other and preferably present a smoothly curved clamping edge from the outer tip that blends with a clamping edge 18a in central regions of the tines 16a. Optionally, the clamping edges of the projections 30a have the same shape in longitudinally transverse reference planes as the wedge shape of the clamping edges 18a along middle sections of the tines 16a.

The projections 30a are adapted to fit in the space between necks of adjacent teeth. More particularly, the projections 30a are adapted to be received between adjacent teeth in an area located directly on an occlusal side (i.e., on a side facing the outer tips of the teeth) of the papilla of the gingiva on its lingual and buccolabial sides. As a result, the projections 30a help shape the sectional matrix band to conform to the original shape of the tooth to be restored, particularly in regions adjacent the neck of the tooth. The projections 30a may also provide an additional wedging force in some instances that helps urge the teeth apart.

A dental matrix clamp 10b according to another embodiment of the invention is illustrated in FIG. 7. The matrix clamp 10b is essentially the same as the matrix clamp 10, except that the matrix clamp 10b has an overall, generally circular configuration in plan view. Additionally, the dental matrix clamp 10b has curved gripping portions 14b that are not parallel to each other and instead form a smoothly curved arc in combination with a coil spring portion 12b.

Additionally, the matrix clamp 10b has clamping edges 18b that are located inwardly of outer end sections of the gripping portions 14b. More particularly, the clamping edges 18b extend along reference axes that lie between the outer end sections of the gripping portions 14b and the coil spring portion 12b.

Figure 8:
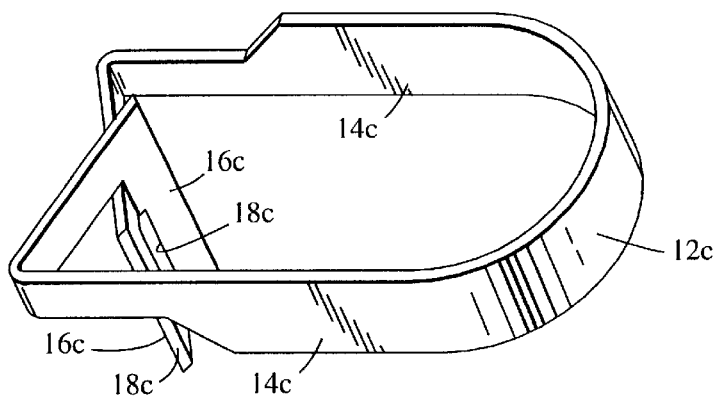
FIG. 8 is a perspective view of a dental matrix clamp constructed in accordance with yet another embodiment of the invention.

A dental matrix clamp 10c according to still another embodiment of the invention is illustrated in FIG. 8. The matrix clamp 10c is essentially the same as the matrix clamp 10 except for the differences as noted below.

As shown in FIG. 8, the matrix clamp 10c has gripping portions 14c with outer end sections that are located forwardly of clamping edges 18c. The clamping edges 18c extend along respective reference axes that lie between the outer end sections of the gripping portions 14c and a coil spring portion 12c.

The configuration of the matrix clamps 10b, 10c may be an advantage in certain instances to facilitate access to the cavity and placement of the restorative material. For example, the inwardly-located clamping edges 18b, 18c may be advantageous when the cavity is located forwardly instead of rearwardly of the tines 16b, 16c. Such use enables the cross-over bars to be located further away from the cavity when the clamp 10b, 10c is in place so that placement of restorative material in the cavity is not unduly impeded.

Figure 9:
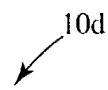
FIG. 9 is a bottom plan view of a dental matrix clamp constructed in accordance with still another embodiment of the invention.

A dental matrix clamp 10d according to another embodiment of the invention is illustrated in FIG. 9. The matrix clamp 10d is essentially the same as the matrix clamp 10 except for the differences noted below.

The dental matrix clamp 10d has a pair of tines 16d, along with a pair of side extensions 32d that are integrally interconnected to the tines 16d. An outer end of each extension 32d has a clamping edge 34d. Each of the tines 16d also has a clamping edge 18d, which optionally is identical or similar to the clamping edge 34d. Optionally, the length of each clamping edge 34d is approximately equal to the width of the side extensions 32d.

The provision of four clamping edges 18d, 34d is useful in instances where a matrix band extends around a substantial majority or optionally around the entirety of the circumference of the tooth to be restored. The clamping edges 18d, 34d cooperate to ensure that the sectional matrix band is tightly held in place against the tooth. Such construction may be an advantage in instances where, for example, large areas such as two or more sides of the tooth must be restored to their original shape.

Figure 10:
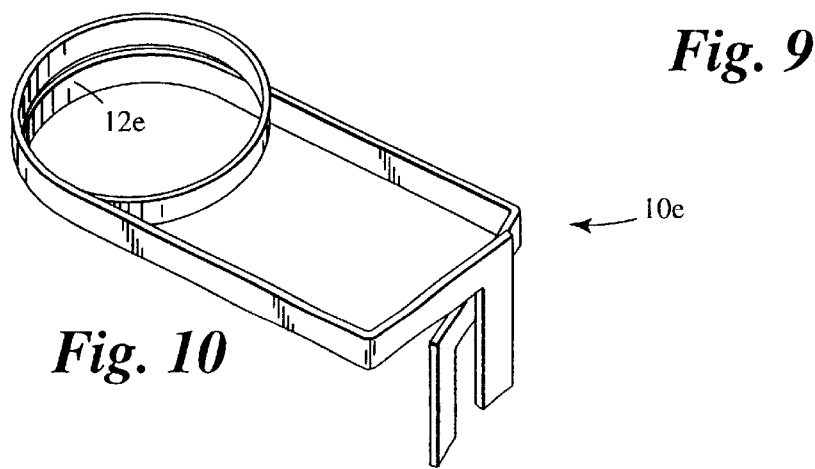
FIG. 10 is a perspective view of a dental matrix clamp according to a further embodiment of the invention.

FIG. 10 is an illustration of a dental matrix clamp 10e according to another embodiment of the invention. The matrix clamp 10e is essentially the same as the matrix clamp 10, except for the differences noted below.

The matrix clamp 10e has a coil spring portion 12e that, in this instance, is comprised of one and one-half coils of spring material. Such construction may be an advantage in reducing fatigue of the matrix clamp material, so that the coil spring portion 12e is more likely to provide a reliable, consistent biasing force over an extended period of time and after multiple uses and resterilizations. Additionally, the coil spring portion 12e may be incorporated in place of the coil spring portion shown in the embodiments depicted in FIGS. 6–9 as well. Moreover, the coil spring portion 12e may include two and one-half or more coils of spring material if desired.

Those skilled in the art may recognize that a number of other modifications and additions may be made to the currently preferred embodiments described above. Accordingly, the invention should not be deemed limited to the embodiments that are described in detail, but instead only by a fair scope of the claims that follow.

What is claimed is:

1. A dental matrix clamp for tooth restoration procedures comprising:

a coil spring portion made of a resilient material;

a pair of spaced apart gripping portions each connected to the coil spring portion, wherein the gripping portions and the coil spring portion extend in a generally common reference plane;

a pair of elongated tines each having an elongated clamping edge, wherein the clamping edges extend along generally parallel paths; and a pair of cross-over bars extending past each other along laterally adjacent paths, each cross-over bar coupling one of the tines to one of the gripping portions, wherein the coil spring portion is biased to urge the clamping edges in directions toward each other, and wherein the clamping edges of the tines extend in directions generally perpendicular to the reference plane to engage opposite sides of an interproximal region between two adjacent teeth in an oral cavity.

2. A dental matrix clamp according to claim 1 wherein the coil spring portion has a generally "U"-shaped configuration.

3. A dental matrix clamp according to claim 1 wherein the clamping edges face each other.

4. A dental matrix clamp according to claim 1 wherein the clamping edges are wedge-shaped.

5. A dental matrix clamp according to claim 1 wherein the clamp is made of a unitary section of metallic material.

6. A dental matrix clamp according to claim 1 wherein the gripping portions have roughened or knurled surfaces.

7. A dental matrix clamp according to claim 1 wherein the gripping portions include a non-slip coating.

8. A dental matrix clamp according to claim 1 wherein the gripping portions have protrusions and/or recesses.

9. A dental matrix clamp according to claim 1 wherein the coil spring portion together with the gripping portions have an overall, generally "U"-shaped configuration.

10. A dental matrix clamp according to claim 1 wherein the coil spring portion together with the gripping portions have an overall, generally circular configuration.

11. A dental matrix clamp according to claim 1 wherein the coil spring portion is a half coil.

12. A dental matrix clamp according to claim 1 wherein the coil spring portion includes more than one coil.

13. A dental matrix clamp according to claim 1 wherein the gripping portions have outer end sections remote from the spring portion and wherein the clamping edges extend along reference axes that lie between the coil spring portion and the outer end sections of the gripping portions.

* * * * *